United States Patent [19]

van der Jagt

[11] Patent Number: Plant 6,085

[45] Date of Patent: Jan. 19, 1988

[54] CHRYSANTHEMUM NAMED "RENDEZ-VOUS"

[75] Inventor: Martinus van der Jagt, Ter Aar, Netherlands

[73] Assignee: Chrysanthemum Breeders Association N.V., Netherlands Antilles

[21] Appl. No.: 775,406

[22] Filed: Sep. 12, 1985

[30] Foreign Application Priority Data

Sep. 14, 1984 [NL] Netherlands ..... CHR 935

[51] Int. Cl.[4] ..... A01H 5/00

[52] U.S. Cl. ..... Plt./76

[58] Field of Search ..... Plt./76, 80

*Primary Examiner*—Robert E. Bagwill

*Attorney, Agent, or Firm*—Parkhurst & Oliff

[57] ABSTRACT

The present invention is a new and distinct variety of Chrysanthemum of a lighter than dawn pink bloom with a rose bengal red center.

3 Drawing Figures

BACKGROUND OF THE INVENTION

The present invention comprises a new and distinct cultivar of Chrysanthemum plant which is a cross of unknown parents. The invention was discovered by Martinus van der Jagt in April, 1983 at Paradijsweg 88, Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

FIG. 1 shows the full bloom of the new cultivar.

FIG. 2 shows various stages of bloom of the new cultivar.

FIG. 3 shows the foliage and stem of the new cultivar.

DESCRIPTION OF THE INVENTION

This new variety of Chrysanthemum is of the botanical classification *Chrysanthemum morifolium* named Rendez-Vous. When grown in the vicinity of Ter Aar, Holland, it has a response time of approximately 8 weeks. This new variety produces medium sized lighter than dawn pink blooms with rose bengal red centers having a 2 week performance. This new variety of Chrysanthemum has been found to retain its distinctive characteristics throughout successive propagations and may be planted under greenhouse conditions in Holland between weeks 1-36.

The following is a description of the plant and characteristics that distinguish it over related known varieties and antecedents:

Bud:
- *Size.*—Medium.
- *Form.*—Round and high.
- *Color.*—Most to orchid purple. R.H.S. 31/3 and R.H.S. 31/2.

Botanical classification: *Chrysanthemum morifolium.*

Bloom:
- *Size.*—Medium.
- *Fully open.*—6 cms.

- *Borne.*—Single, sometimes several.
- *Stems.*—Medium to weak.
- *Form.*—Decorative.
- *Permanence.*—Appr. 12-14 days.

Color:
- *Center of flower.*—Rose bengal red, R.H.S. 25.
- *Base of petals.*—Lighter than dawn pink, near R.H.S. 523/3.
- *Inside of petals.*—Lighter than dawn pink, near R.H.S. 523/3.
- *Reverse of petals.*—Lighter than dawn pink, near R.H.S. 523/3.
- *Outer petals.*—Lighter than dawn pink, near R.H.S. 523/3.
- *Tonality from a distance.*—A double colored decorative. Most of the petals are lighter than dawn pink. The center is a rose bengal red.
- *Discoloration.*—Some to more white.

Petals:
- *Texture.*—Decorative flower. Incurving petals in the center, straight to reflexing petals to the edge.
- *Number.*—Besides the incurved center part appr. 78-85.
- *Arrangement.*—Imbricated.
- *Persistence.*—Medium to strong.
- *Fragrance.*—Normal.

Reproductive organs:
- *stamens.*—Very small.
- *Pollen.*—Few.
- *Styles.*—Columnar.
- *Length.*—Medium.
- *Stigmas.*—Small.
- *Ovaries.*—Enclosed in calyx.

Plant:
- *Form.*—Herbaceous.
- *Growth.*—Medium.
- *Height.*—Medium.
- *Peduncle.*—Medium to weak.

Foliage:
- *Color.*—Medium.
- *Size.*—Medium to large.
- *Quantity.*—Normal.
- *Shape.*—Pointed.
- *Texture.*—Normal.
- *Ribs and veins.*—Light and sharp.
- *Edge.*—Undulated to deeply undulated.

*Leaf underside.*—Rough.
*Leaf upperside.*—Rough.

In the description above, color references are made to The Horticultural Colour Chart I & II issued by The British Colour Council in collaboration with The Royal Horticultural Society, Copyright Robert F. Wilson, Vol I, 1938; Vol II, 1941, printed by Henry Stone & Son, Ltd., Banbury, England.

I claim:

1. A new and distinctive variety of Chrysanthemum named Rendez-Vous, as described and illustrated in the foregoing specification and accompanying drawings.

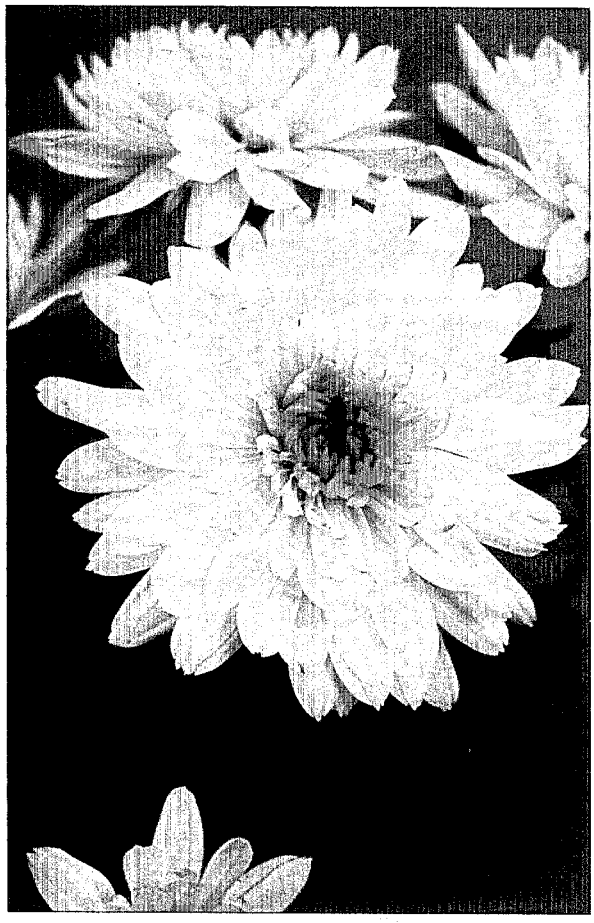

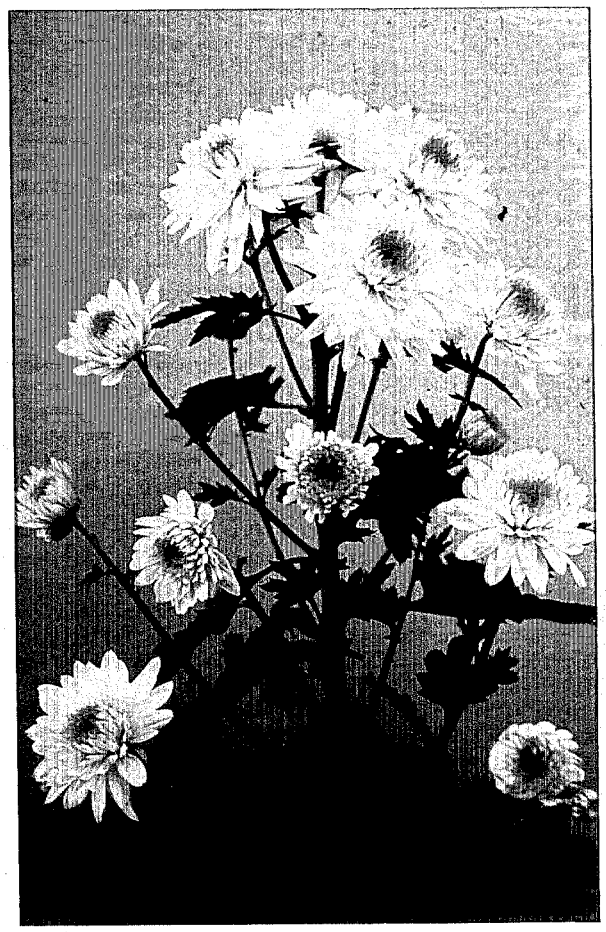

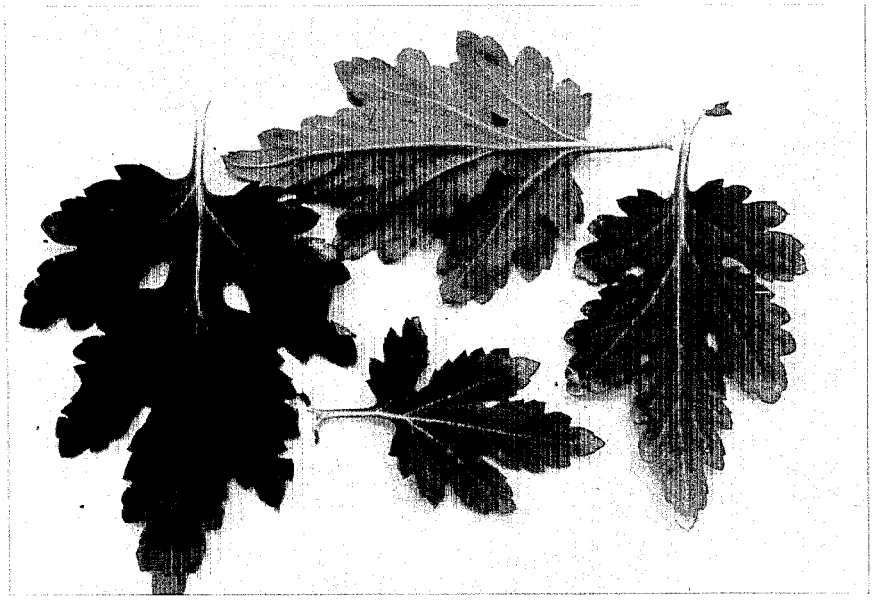

* * * * *